United States Patent [19]

Baldwin et al.

[11] Patent Number: 5,663,046
[45] Date of Patent: Sep. 2, 1997

[54] SYNTHESIS OF COMBINATORIAL LIBRARIES

[75] Inventors: John J. Baldwin, Gwynedd Valley, Pa.; Eric G. Horlbeck, Plainsboro, N.J.

[73] Assignee: Pharmacopeia, Inc., Princeton, N.J.

[21] Appl. No.: 263,804

[22] Filed: Jun. 22, 1994

[51] Int. Cl.$^6$ .................................................. G01N 33/53
[52] U.S. Cl. ................................. 435/6; 435/71; 436/501; 436/518; 436/531; 436/533; 530/333; 530/334; 536/18.5; 536/25.3
[58] Field of Search .......................... 435/6, 7.1; 530/333, 530/334; 536/18.5, 18.6, 25.3, 25.31, 25.32, 25.4; 936/501, 518, 537, 533

[56] References Cited

FOREIGN PATENT DOCUMENTS 9322684  11/1993  WIPO .

OTHER PUBLICATIONS

Ohlmeyer et al. PNAS, vol. 90 pp. 10922–10926 (1993) "Complex synthetic chemical libraries indexed with molecular tags".

Needels et al. PNAS, vol. 90, pp. 10700–10704 (1993) "Generation and screening of an oligonucleotide–encoded synthetic peptide library".

DeWitt et al. PNAS, vol. 90, pp. 6909–6913 (1993) "'Diversomers'; An approach to nonpeptide, nonoligomeric chemical diversity".

R.M. Baum.C&EN, 20–25, Feb. 7, 1994.

Furka et al., "Cornucopia of Peptides by Synthesis", Abstr. 14th Int. Cong. of Biochem., Prague Czechoslovakia, vol. 5, p. 47 (1988).

Furka et al., "More Peptides by Less Labour", Abstr. 10th Int. Sym. on Med. Chem., Budapest, Hungary p. 288 (1988).

Gallop et al. Jour. Med. Chem., vol. 37, No. 9, 1233–1251, (1994).

Bernardo and Smith, Bayesian Theory, pp. 115 & 428, John Wiley & Sons (1994).

Lothar Sachs, Applied Statistics, 171–174, Springer–Verlag (1984).

*Primary Examiner*—Lora M. Green
*Attorney, Agent, or Firm*—Heslin & Rothenberg, P.C.

[57] ABSTRACT

Directly dividing the contents of each sub-pool into the sub-pools for the next step in the synthetic scheme for producing a combinatorial library reduces the standard deviation, σ, relative to the standard deviation of the split synthesis method for producing such libraries.

8 Claims, No Drawings

SYNTHESIS OF COMBINATORIAL LIBRARIES

BACKGROUND OF THE INVENTION

There is interest in methods for the synthesis of large numbers of diverse compounds which can be screened for various possible physiological or other activities. Techniques have been developed in which one adds individual units sequentially as part of the chemical synthesis to produce all or a substantial number of the possible compounds which can result from all the different choices possible at each sequential stage of the synthesis. Numerous strategies have been devised for producing such combinatorial libraries (R. M. Baum, Combinatorial Approaches Provide Fresh Leads for Medicinal Chemistry, C&EN, 20–25, Feb. 7, 1994). Common to many of these strategies is a technique known as split synthesis (Furka et al., "Cornucopia of Peptides by Synthesis", Abstr. 14th Int. Cong. of Biochem., Prague Czechoslovakia, Vol. 5, p 47 (1988) and "More Peptides by Less Labour", Abstr. 10th Int. Sym. on Med. Chem., Budapest, Hungary p 288 (1988)), which essentially comprises dividing a first pool of material into sub-pools, treating these sub-pools so as to effect a change in the material, mixing the sub-pools into a second pool, and then again dividing the changed material into a new set of sub-pools for further treatment. This process is iterated until the desired end products are produced. Ideally, every theoretical member of the library is produced by this synthesis on solid supports, where each solid support holds an individual member, and these members are present in equal number, i.e., in the final pool there is an equal number of members for every possible combination of reactions. However, a perfectly even splitting is not achieved and this can lead to the non-production of some members and an over or under production of others. Over or under production of members can lead to other errors. For example, in deconvolution analysis of combinatorial libraries over or under representation of library members can be misinterpreted as indicating strong or weak compounds, e.g., in a binding assay, and result in the further elaboration of uninteresting compounds. One way to reduce the first of these possibilities (non-production) is to design for an excess amount of each member in these syntheses, typically 10–1000 fold redundancy. However, this approach does not affect the over or under production of certain members. Even with redundancy there is a calculable error ($\sigma$) from the ideal. Reduction of this error is desirable.

SUMMARY OF THE INVENTION

It has now been found that directly dividing the contents of each sub-pool into the sub-pools for the next step in the synthetic scheme reduces $\sigma$ relative to the $\sigma$ of split synthesis.

DETAILED DESCRIPTION OF THE INVENTION

The present invention relates to a method for producing combinatorial libraries of compounds. These libraries of compounds can include 1) biopolymers such as peptides, oligonucleotides, and oligosaccharides, 2) combinations of peptides, oligonucleotides, and oligosaccharides, 3) non-oligomers such as heterocyclic, aromatics, alicyclics, aliphatics, and combinations thereof, and 4) any other compounds amenable to combinatorial synthesis. Non-oligomers includes benzodiazepines, prostaglandins, sulfonamides, pyrrolidines, etc. Combinatorial libraries of compounds are produced by partitioning a set of particles, i.e., the solid supports, into a first group of reaction vessels wherein they uniquely treated, re-partitioning the treated particles via a common pool into a second group of reaction vessels wherein they are again uniquely treated, and repeating this process until the desired combinatorial library is produced. The unique treatment in each vessel is typically the addition, as by chemical means, of some moiety, each such treatment being selected so that at the end of the process all the members of the combinatorial library will have been produced. The method of this invention, which is referred to herein as direct dividing, comprises directly dividing among the reaction vessels to be used for the next step, in substantially equal amounts, the particles in each reaction vessel at the end of the previous step. Unlike split synthesis, at no time during the synthesis are the treated particles combined into a common pool. In this way, each reaction vessel in a next step will contain substantially the same number of identical particles from each reaction vessel in the previous step. The procedure may be repeated, typically 1–5 times, until the synthesis is complete. Preferably, at the end of the synthesis every member of the library is represented in equimolar amounts.

Directly dividing the reaction supports offers a significant advantage over split synthesis, i.e., pooling and dividing, since it distributes more evenly the different compounds created at each step. This means that the actual number of solid supports holding non-identical library members will be closer to the theoretical minimum number of supports. As a result there will be fewer cases of compounds not represented, over-represented, or under-represented in the final pool. Consequently, this reduces the redundancy necessary to assure a minimum expected representation of each possible compound in the library. For example, 10,000 beads are equally divided into 100 reaction vessels. A different bifunctional synthon is allowed to react with the solid supports in each reaction vessel. Under split synthesis, the solid supports are combined and then equally divided into another 100 reaction vessels where they are allowed to react with a second synthon. A combinatorial analysis of this approach shows that 36.4% of the possible products are not produced at all and 26.4% of the possible products are over-represented. If the number of beads is increased to 30,000 (i.e., 3-fold redundancy), the number of products not represented is reduced to 4.8% but there is still be a significant number of products over-represented (35.3%) and under-presented (42.1%). In contrast, using the direct division method of this invention, every member of the combinatorial library is produced in equal proportion using either 10,000 or 30,000 beads.

The structure of each compound on a given solid support in a combinatorial library is determined by its reaction history, i.e., by the identity of the reaction vessels for each of its starting materials and intermediates. Ideally, each possible compound would be represented in the final mixture in a pre-determined mount. This will deviate based on a statistical variation inherent to the splitting paradigm In order for the theoretical outcome to occur, at each reaction step, each reaction vessel must contain a pre-determined amount of every compound produced up to that point. However, when a mixture of intermediates obtained by pooling each subdivision from the previous step is divided into the reaction vessels for the next step in the synthesis, there is a statistical variation in the intermediates which go into each vessel. Such variation is inherent for both split synthesis and direct division after the second synthetic step. However, the variation ($\sigma$) will be significantly less for direct dividing than for split synthesis.

Each time that splitting occurs, the probability that x members of a given compound will be drawn into a given vessel is described by the hypergeometric distribution, $$P(x) = \frac{\binom{s}{x}\binom{n-s}{d-x}}{\binom{n}{d}},$$

wherein s is the number of members of the given compound in the original vessel, n is the total number of components (i.e., (compounds). (redundancy)) in the original vessel, and d is the number of components drawn from the original vessel into the given vessel.

The expected number of members of a given compound drawn is $$\bar{x} = \frac{ds}{n}$$

(where $\bar{x}$ is the mean of x). A measure of how much x varies about the mean is given by the variance, $$\sigma^2 = \frac{d(n-d)s(n-s)}{n^2(n-1)}.$$

The following analysis applies under these preconditions: 1) there are more than one reaction vessel at each of step i and i+1; 2) there are at least as many intermediates as vessels at step i; and 3) there are more than one intermediate that have been through the path of interest up to step i. When a split occurs, if $s_i$ is the number of intermediate compounds that have been through a particular synthetic path up and including step i, then $P(s_{i+1})$ is the probability distribution of those intermediates that continue on a particular path up to step i+1. Both split synthesis and direct dividing will have such a distribution for apportioning the intermediates from step i to step i+1 given $s_i$ intermediates of interest in step i. The difference will be the appropriate values of n and d.

Now let $b_i$=number of vessels in step i.

For split synthesis:

n=total number of beads in the mixing container=B, and d=number of beads drawn into each container on level i+1=$B/b_{i+1}$.

This leads to a variance of $$\sigma^2_{split} = \frac{\frac{B}{b_{i+1}}\left(B - \frac{B}{b_{i+1}}\right)s(B-s)}{B^2(B-1)} = \frac{\left(1 - \frac{1}{b_{i+1}}\right)s(B-s)}{b_{i+1}(B-1)}$$

For direct divide synthesis:

n=total number of beads in level i container=$B/b_i$, and d=number of beads drawn from level $B/(b_i\, b_i+1)$.

This leads to a variance of $$\sigma^2_{direct} = \frac{\frac{B}{b_i b_{i+1}}\left(\frac{B}{b_i} - \frac{B}{b_i b_{i+1}}\right)s\left(\frac{B}{b_i} - s\right)}{\left(\frac{B}{b_i}\right)^2 \left(\frac{B}{b_i} - 1\right)} =$$

-continued $$\frac{\left(1 - \frac{1}{b_{i+1}}\right)s(B - b_i s)}{b_{i+1}(B - b_i)}$$

The smaller the variance, the more evenly distributed the different compounds will be on step i+1. To show which variance is smaller we take the difference, $$\sigma^2_{split} - \sigma^2_{direct} = \frac{\left(1 - \frac{1}{b_{i+1}}\right)s_i}{b_{i+1}}\left(\frac{B - s_i}{B - 1} - \frac{B - s_i b_i}{B - b_i}\right)$$

$$= \frac{\left(1 - \frac{1}{b_{i+1}}\right)s_i}{b_{i+1}}\left(\frac{B(s_i - 1)(b_i - 1)}{(B-1)(B - b_i)}\right)$$

which is greater than zero if $b_i>1, b_{i+1}>1, s_i>1, B>b_i$; i.e., the variance of direct dividing will always be smaller than the variance of split synthesis.

The present invention also relates to combinatorial chemical libraries of compounds, optionally encoded with tags, and to the use of these libraries in assays to discover biologically active compounds. The invention also relates to methods for their preparation, intermediates, and to methods and pharmaceutical formulations for using these compounds in the treatment of mammals, especially humans.

One embodiment of the invention is the use of a combinatorial library of compounds generated by the direct divide method in assays to discover biologically active compounds (ligands). Thus, an aspect of the invention is a method of identifying a compound having a desired characteristic which comprises synthesizing a combinatorial library and testing the compounds of this library and the ligands, either attached to the solid support or detached therefrom, in an assay which identifies compounds having the desired characteristic. A further embodiment of the invention is determining the structure of any compound so identified.

Definitions

The following abbreviations have the indicated meaning:

DEAD=diethylazodicarboxylate
DCM=dichloromethane=methylene chloride
DIC=diisopropylcarbodiimide
DMAP=4-N,N-dimethylaminopyridine
DMF=N,N-dimethylformamide
EDT=ethane dithiol
FACS=fluorescence activated cell sorting
Fmoc=9-fluorenylmethoxycarbonyl
HOBt=N-hydroxybenzotriazole
Me=methyl
PEG=polyethylene glycol
Ph=phenyl
r.t.=room temperature
sat'd=saturated
t-=tertiary
TFA=trifluoroacetic acid
THF=tetrahydrofuran Any identification method may be used with this invention. Thus, a strategy using chemical entities, i.e., tags, or a deconvolution, or "mimotope strategy", method such as taught by Geysen et al., J. Immunol Methods, 102, 259–274 (1987) and Geysen et al., Mol. Immunol. 23, 709–715

(1986) may be used. The tags may be peptides (e.g., Kerr et al., J. Amer. Chem. Soc., 115, 2529–2531 (1993) and Nikolaiev et al., Pept. Res., 6, 161–170 (1993)), oligonucleotides (e.g., Needles et al., Proc. Natl. Acad. Sci. USA, 90, 10700–10704 (1993), Lerner et al., PCT Appli. WO 93/20242, and Brenner and Lerner Proc. Natl. Acad. Sci. USA, 89, 5181–5183 (1992)), or electrophoric tags (e.g., Ohlmeyer et al., Proc. Natl. Acad. Sci. USA, 90, 10922–10926 (1993) and Still et al., PCT Appli. WO 94/08051). Preferably, the electrophoric tags are chemical entities which possess several properties: they must be detachable from the solid supports, preferably by photolysis or oxidation; they must be individually differentiable, and preferably separable; they must be stable under the synthetic conditions; they must be capable of being detected at very low concentrations, e.g., $10^{-18}$ to $10^{-9}$ mole; they should be identifiable with readily-available equipment which does not require sophisticated technical capabilities to operate; and they should be relatively economical. The tags may be structurally related or unrelated, e.g., a homologous series, repetitive functional groups, related members of the Periodic Chart, different isotopes, combinations thereof, and the like. At the end of the combinatorial synthesis, to each solid support, there will usually be attached at least 0.01 femtomol, usually 0.001–50 pmol, of each tag. The tags may be aliphatic, alicyclic, aromatic, heterocyclic, or combinations thereof. Distinguishing features may be the number of repetitive units, such as methylene groups in an alkyl moiety; alkyleneoxy groups in a polyalkyleneoxy moiety; halo groups in a polyhalo compound; α- and/or β-substituted ethylene groups where the substituents may be alkyl groups, oxy, carboxy, amino, halo, or the like; isotopes; etc.

The materials upon which the combinatorial syntheses of the invention are performed are referred to as solid supports, beads, and resins. These terms are intended to include:

beads, pellets, disks, fibers, gels, or particles such as cellulose beads, controlled pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, and glass particles coated with hydrophobic polymer, etc., i.e., material having a rigid or semi-rigid surface.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R) or (S), or as (D) or (L) for amino acids. The present invention is meant to comprehend all such possible diastereomers as well as their racemic and optically pure forms. Optically active (R) and (S), or (D and L), isomers may be prepared using chiral synthons or chiral reagents, or resolved using conventional techniques. When the compounds described herein contain olefinic double bonds, and unless specified otherwise, it is intended to include both E and Z geometric isomers.

Utilities

These compounds may also be used as libraries for discovering new lead structures by evaluation across an array of biological assays, including the discovery of selective inhibition patterns across isozymes. These libraries are thus tools for drug discovery; i.e., as a means to discover novel lead compounds by screening the libraries against a variety of biological targets and to develop structure-activity relationships in large families of related compounds. The libraries may be tested with the ligands attached to the solid supports or the individual compounds may be detached prior to evaluation. With the compounds of the combinatorial library, screening assays such as FACS sorting and cell lawn assays may be used. When a ligand is detached prior to evaluation, its relationship to its solid support is maintained, for example, by location within the grid of a standard 96-well plate or by location of activity on a lawn of cells. The solid support associated with bioactivity or the solid support related to the detached ligand may then be decoded to reveal the structural or synthetic history of the active compound (Ohlmeyer et al., Proc. Natl. Acad. Sci. USA, 90, 10922–10926, December 1993).

The following schemes demonstrate application of the method of the invention to the preparation of a tagged combinatorial library of sulfonamides represented by Formula I:

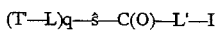

wherein:

§ is a solid support;

T'—L— is of the Formula:

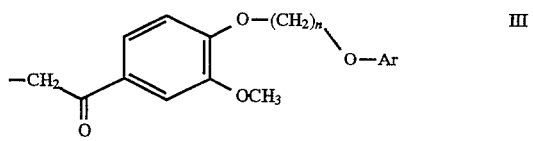

wherein n=3–12 when Ar is pentachlorophenyl and n=4–6 when Ar is 2,4,6-trichlorophenyl;

q is 3–13;

—L'—II' a ligand/linker residue;

—L'— is

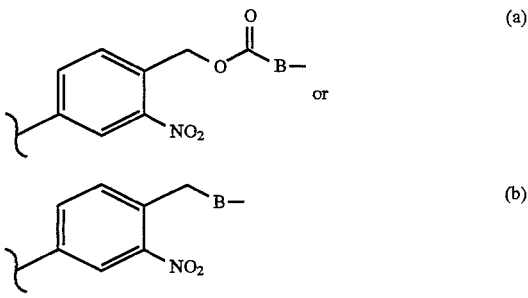

wherein the left-hand bond as shown is the point of attachment to the solid support and the right hand bond is the point of attachment to the ligand, and B is O or NH, with the proviso that in (b) B is NH when attached to a carbonyl group in the ligand; and II is represented by the formula

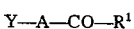

wherein $R^1$, A, and Y are as defined in Table 1—1, 1-2, and 1-3, respectively.

At each step in the synthesis each solid support upon which a compound is being synthesized is uniquely tagged to define the particular chemical event(s) occurring during that step. The tagging is accomplished using identifiers such as those of Formula IV, which record the sequential events to which the support is exposed during the synthesis, thus providing a reaction history for the compound produced on each support. The identifiers are used in combination with one another to form a binary or higher order encoding scheme permitting a relatively small number of identifiers to encode a relatively large number of reaction products.

In carrying out the synthesis, one begins with at least $4 \times 10^4$, and generally not exceeding $10^{15}$ solid supports. Depending on the pre-determined number of $R^1$ choices for the first step, one divides the supports accordingly into as many containers. The appropriate reagents and reaction conditions are applied to each container and the combination of identifiers which encode for each $R^1$ choice is added and attached. Depending on the chemistries involved, the tagging may be done prior to, concomitantly with, or after the reactions which comprise each choice. As a control, sample supports may be picked at any stage and a portion of their tags detached and decoded to verify that the correct tags are bound to the sample supports. As needed, one may wash the beads free of any excess reagents or by-products before proceeding. At the end of each step, the supports in each container are divided into as many containers as pre-determined for the number of A choices for the second step in the synthesis. Direct dividing is accomplished by, e.g., weighing or by the isopyctic method of pipetting aliquots from an isobuoyant suspension of supports. This procedure of dividing, reacting, tagging, and direct dividing is repeated until the combinatorial synthesis is completed.

Scheme 1

Functionalized supports such as amino-functionalized or hydroxy-terminating PEG grafted polystyrene beads are equally divided into a pre-determined number of reaction vessels and are reacted with either a) a cleavable linker/ligand element which has been pre-formed to generate 2 when the detached ligand element terminates in OH or b) a cleavable linker, followed by reaction with a ligand element to generate 3 in the case when the detached ligand element terminates in COOH. Compounds 2 and 3 are then treated with piperidine/DMF to de-protect the amino group of the ligand element $R^1$ to yield 4 (Scheme 1, step (c)). Unique tagging of the supports in each reaction vessel is achieved with combinations of identifiers encoded in a binary scheme, e.g., as depicted in Table 1–1 for seven choices of R1. The identifiers are attached by adding a solution of the identifiers (in a 5% wt./wt. identifier:solid support ratio) to a batch of supports suspended in $CH_2Cl_2$ and shaking the mixture for 30 min. A dilute solution of rhodium trifluoroacetate dimer is added and the mixture is immediately shaken. The mixture is continued to be shaken overnight and then washed in $CH_2Cl_2$.

Scheme 2

The compounds 4 are directly divided into a pre-determined number of reaction vessels, each of which is treated with one reagent corresponding to ligand element A, in the presence of HOBt/DMF to produce 5. The reaction vessels are then treated with piperidine/DMF to de-protect the terminal amino group, yielding 6. Unique tagging of the supports in each reaction vessel is achieved with combinations of additional identifiers encoded in a binary scheme, e.g., as depicted in Table 1–2 for 31 choices of A.

Scheme 3

The compounds 6 are then directly divided into a pre-determined number of reaction vessels each of which is treated with one reagent corresponding to ligand element Y in the presence of solvents such as $CH_2Cl_2$ and DMF, and, when required, condensation reagents such as DIC, acylation catalysts such as DMAP, and bases such as triethylamine to produce 7. Unique tagging of the supports in each reaction vessel is achieved with combinations of additional identifiers encoded in a binary scheme, e.g., as in Table 1–3 for 31 choices of Y. Compound 7 is then either exposed to UV light (~360 nm) in a lower alkanol such as MeOH to cleave the protected form of the compounds of Formula II from the support/linker complex or first treated with TFA/thioanisole/EDT to remove the protecting groups on the $R^2$ sidechains and then exposed to UV light in a lower alkanol such as MeOH to cleave compound II.

SCHEME 1
ADDITION OF $R^1$ a. Carbonate-linked Moieties

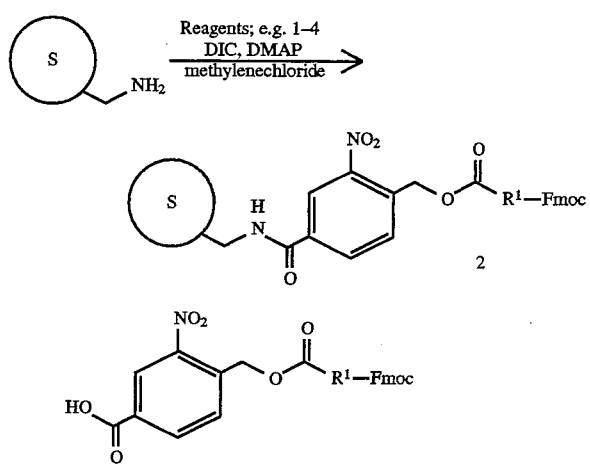

R = Reagents 1–4

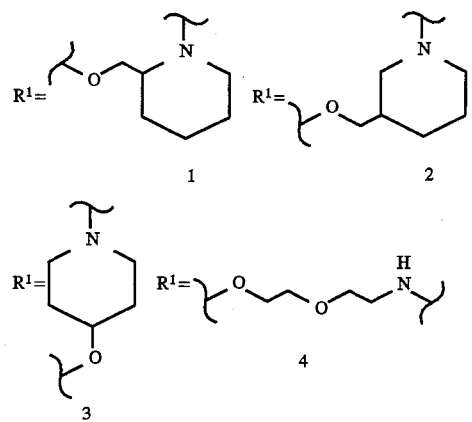

b. Ester-linked Moieties

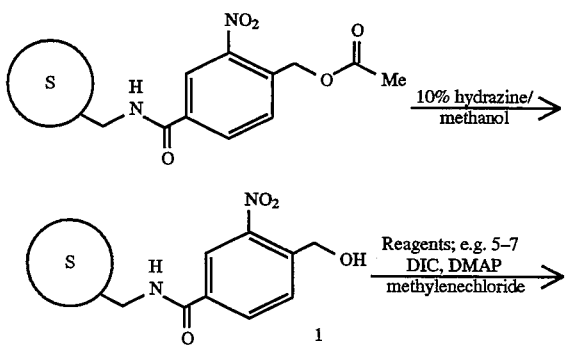

-continued
SCHEME 1
ADDITION OF R¹
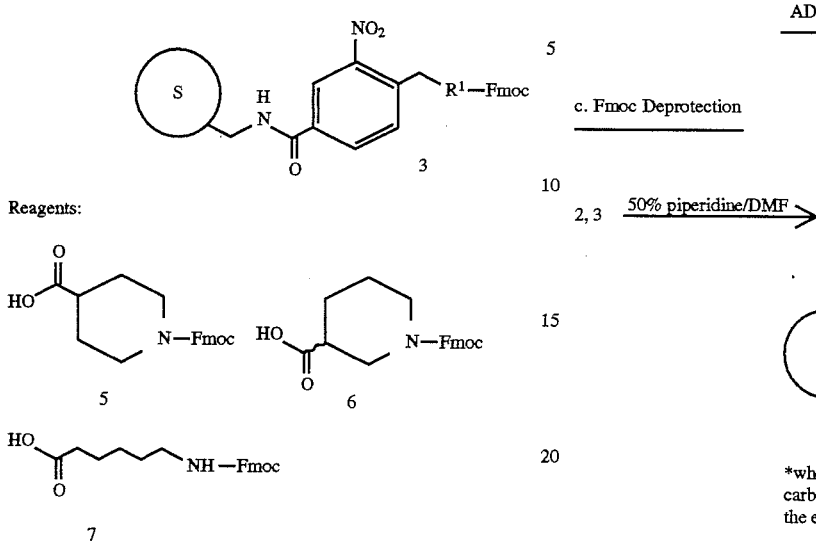
Reagents:
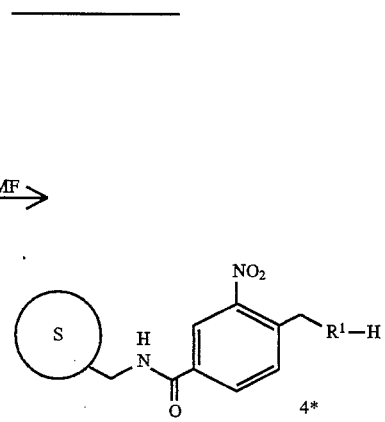
-continued
SCHEME 1
ADDITION OF R¹
c. Fmoc Deprotection
2, 3 →(50% piperidine/DMF)→
*where R¹ includes the carbonate linkage in 2 and the ester linkage in 3
SCHEME 2
ADDITION OF A
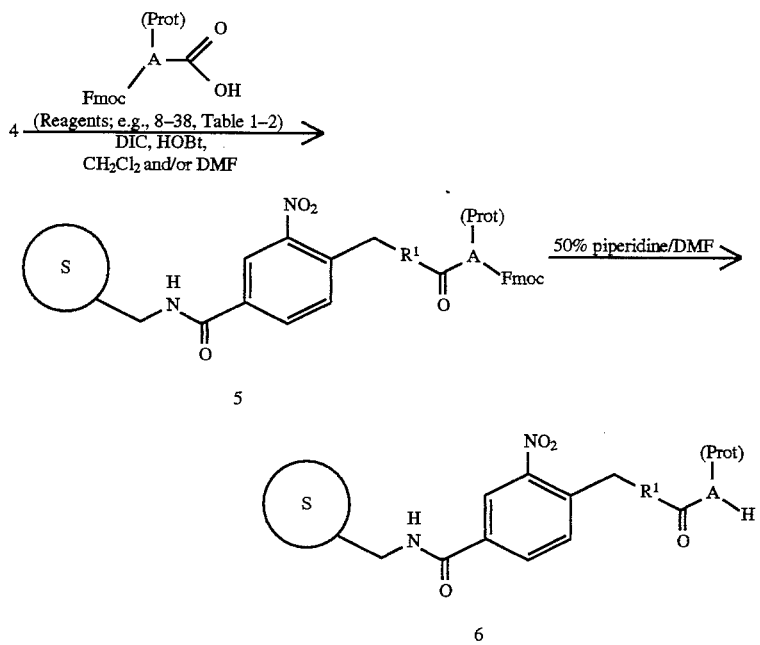
(Prot) = optional, non-Fmoc, base stable sidechain protecting group

SCHEME 3
ADDITION OF Y

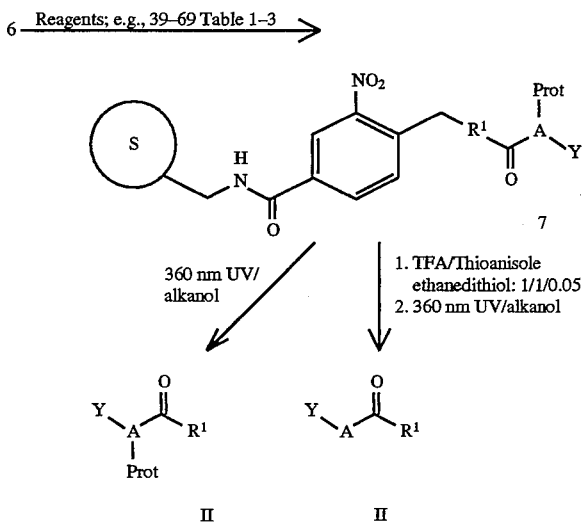

The invention is further defined by reference to the following examples, which are intended to be illustrative and not limiting.

PREPARATION 1 IDENTIFIERS

Thirteen compounds of the general formula:

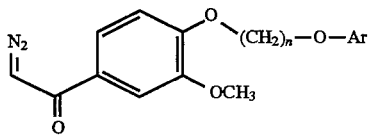

wherein:

n=3–12 and Ar is pentachlorophenyl or
n=4–6 and Ar is 2,4,6-trichlorophenyl were prepared according to Scheme 4 and the following illustrative example.

a) Methyl vanillate (0.729 g, 4.0 mmole), 1-hydroxy-9-(2,3,4,5,6-pentachlorophenoxy)nonane (1.634 g, 4.0 mmole) and triphenylphosphine (1.258 g, 4.8 mmole) were dissolved in 20 mL dry toluene under argon. DEAD (0.76 mL, 0.836 g, 4.8 mmole) was added dropwise and the mixture was stirred at 25° C. for one hr. The solution was concentrated to half volume and purified by flash chromatography eluting with DMC to give 1.0 g (1.7 mmole, 43%) of the product as a white crystalline solid.

b) The methyl ester from Step (a) (1.0 g, 1.7 mmole) was dissolved in 50 mL THF, 2 mL water was added, followed by LiOH (1.2 g, 50-mmole). The mixture was stirred at 25° C. for one hr. then refluxed for 5 hr. After cooling to 25° C., the mixture was poured onto ethyl acetate (200 mL) and the solution was washed with 1M HCl (3×50 mL) then sat'd aq. NaCl (1×50 mL) and dried over sodium sulfate. The solvent was removed and the crude acid azeotroped once with toluene.

c) The crude material from Step (b) was dissolved in 100 mL toluene, 10 mL (1.63 g, 14 mmole) thionyl chloride was added, and the mixture was refluxed for 90 min. The volume of the solution was reduced to approx. 30 mL by distillation, then the remaining toluene was removed by evaporation. The crude acid chloride was dissolved in 20 mL dry DCM and cooled to −70° C. under argon and a solution of approx. 10 mmole diazomethane in 50 mL anhydrous ether was added. The mixture was warmed to r.t. and stirred for 90 min. Argon was bubbled through the solution for 10 min., then the solvents were removed by evaporation and the crude material was purified by flash chromatography, eluting with 10–20% ethyl acetate in hexane. The diazoketone (0.85 g, 1.4 mmole, 82% yield over three steps) was obtained as a pale yellow solid.

The other 12 identifiers of Formula IV were prepared by analogous synthetic routes, steps (a), (b), and (c).

In the synthesis of Example 1, the 13 identifiers were used to encode the combinatorial library. In Step 1, pentachlorophenyl identifiers where n=10–12 (abbreviated $C_{10}Cl_5$, $C_{11}Cl_5$, and $C_{12}Cl_5$) were used in the following binary encoding scheme: 001=(n=12), 010=(n=11) and 100=(n=10). In Step 2, pentachlorophenyl identifiers where n=5–9 (abbreviated $C_5Cl_5$, $C_6Cl_5$, $C_7C_{15}$, $C_8C_{15}$, and $C_9C_{15}$) were used encoded as follows: 00001=(n=9), 00010=(n=8), 00100=(n=7), 01000=(n=6) and 10000=(n=5). In Step 3, pentachlorophenyl identifiers where n=3–4 (abbreviated $C_3Cl_5$ and $C_4Cl_5$) were used and encoded as follows: 00001=(n=4), 00010=(n=3). Also in Step 3, trichlorophenyl identifiers where n=4–6 (abbreviated $C_4Cl_3, C_5C_3$, and $C_6Cl_3$) were used and encoded as follows: 00100=(n=6), 01000=(n=5), and 10000=(n=4).

Thus, in Step 1 reagent 3 (Table 1-1) is encoded "011" which represents tagging this choice in the synthesis with the two pentachlorophenyl identifiers where n=11 and 12. Likewise, in Step 3 reagent 52, (Table 1-3) is encoded "01110" which represents tagging this choice in the synthesis with the pentachlorophenyl identifier where n=3 and the two trichlorophenyl identifiers where n=5 and 6.

SCHEME 4
IDENTIFIERS

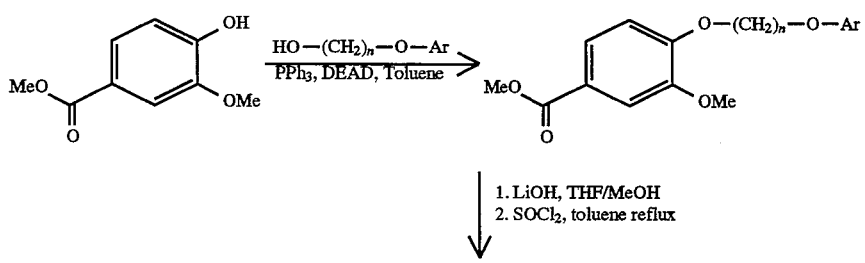

-continued
SCHEME 4
IDENTIFIERS

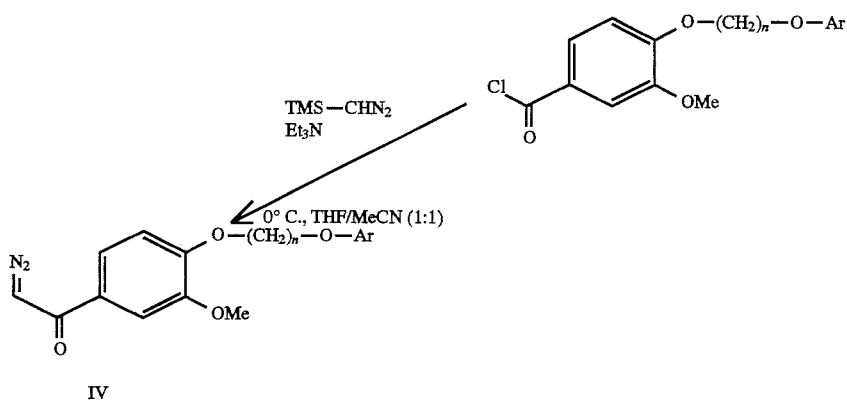

PREPARATION 2 t-BUTYL-4-(HYDROXYMETHYL)-3-NITROBENZOATE t-Butyl 4-(acetoxymethyl)-3-nitrobenzoate was prepared as described by Barany and Albericio, *J. Am. Chem. Soc.* 1985, 107, 4936–4942. However, the reference's final procedure for hydrazinolysis of the acetate using hydrazine hydrate in $CHCl_3$ at 25° C. to produce t-butyl 4-(hydroxymethyl)-3-nitrobenzoate, which is the t-butyl ester pre-cursor of the photocleavable linker used herein, was changed to hydrazinolysis using hydrazine hydrate in MeOH at 25° C. to produce the desired hydroxymethyl final product in near quantitative yield.

This new hydrazinolysis procedure was also used to produce the photocleavable linker when attached to Tenta-Gel S $NH_2$ resin.

t-Butyl 4-(hydroxymethyl)-3-nitrobenzoate:

To a solution of 14.1 g (47.7 mmol, 1.00 eq.) of t-butyl 4-(acetoxymethyl)-3-nitrobenzoate in MeOH (200 mL) was added 27.0 mL (477 mmol, 10.0 eq.) of hydrazine hydrate (55% hydrazine). The resulting yellow solution was stirred at 25° C. for 4 hr. EtOAc (250 mL) and saturated aq. NaCl (85 mL) were added, and the organic layer collected after shaking. The organic layer was washed further with saturated aq. NaCl (2×85 mL), and then dried ($MgSO_4$). Removal of volatiles in vacuo gave the product in 93% yield as yellow crystals.

TentaGel S $NH_2$-attached 4-(hydroxymethyl)-3-nitrobenzamide: See Example 1, Step 1a.

The reaction is represented in Scheme 5.

SCHEME 5
HYDRAZINOLYSIS

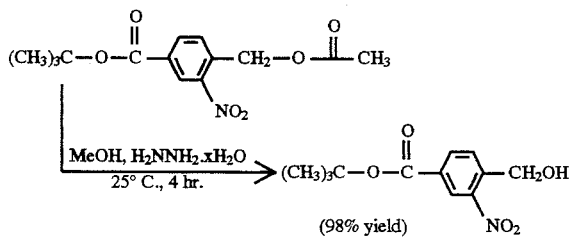

(98% yield)

EXAMPLE 1

6727 COMPOUND LIBRARY

Step 1 a) Preparation of ester-linked resin batches

TentaGel S $NH_2$, (10 g, 2.9 mmole, 0.29 mmole/g) was suspended in 60 mL methylenechloride. 4-acetoxymethyl-3-nitrobenzoic acid (2.77 g, 11.6 mmole, 4 eq), DMAP (1.42 g, 11.6 mmole, 4 eq) and DIG (1.81 mL, 1.46 g, 11.6 mmole, 4 eq) was added in that order. The mixture was agitated at 25° C. with a wrist action shaker for 5 hours, at which time the resin gave a negative Kaiser test. The derivatized resin was washed (methylenechloride 5×50 mL, isopropanol 5×50 mL, then methylenechloride 5×50 mL), dried in vacuo and stored in the dark.

The acetoxymethyl resin above was washed with methanol (1×150 mL), then suspended in 150 mL 10% hydrazine/methanol. The resin was agitated at 25° C. for 44 hours, filtered, then washed (methanol, 5×100 mL, then methylene chloride, 5×100 mL) and dried in vacuo.

Three batches of the above hydroxymethyl resin (3 g each, 0.84 mmole, 0.28 mmole/g) were placed in 100 mL synthesis vessels and each was suspended in 60 mL dichloromethane. One of N-Fmoc isonipecotic acid (0.885 g, 2.52 mmole, 3 eq), N-Fmoc nipecotic acid (0.885 g, 2.52 mmole, 3 eq), and N-Fmoc-ε-amino caproic acid (0.890 g, 2.52 mmole, 3 eq) was added to each of the three batches. DMAP (0.03 1 g, 0.252 mmole, 0.3 eq) and then DIC (0.4 mL, 0.318 g, 2.52 mmole, 3 eq) was added to each and the resin batches were agitated at 25° C. for 22 hours. The resin batches were filtered, washed (methylenechloride (5×50 mL) and isopropanol (2×50 mL), then methylenechloride (5×50 mL)), and dried in vacuo.

b) Preparation of carbonate-linked resin batches

N-Fmoc-2-hydroxymethylpiperidine (1.35 g, 4 mmole, 1.eq) was dissolved in 20 mL methylenechloride and cooled to 0° C. Phosgene (8 mL, 2M solution in toluene, 16 mmole, 4 eq) was added followed by 2,6-lutidine (1.86 mL, 1.71 g, 4 eq), then the mixture was stirred for 30 min. The mixture was concentrated on a rotary evaporator to give a viscous slurry and this residue was redissolved in 30 mL methylenechloride (the solution contained some undissolved solid). <sup>t</sup>Butyl 4-hydroxymethyl-3-nitrobenzoate (0.51 g, 2 mmole, 0.5 eq) was added and the mixture was stirred at 25° C. for 2 hours. The crude reaction mixture was poured onto 200 mL ethyl acetate and this solution was washed with 1M HCl (2×100 mL), sat'd aq. $NaHCO_3$ (2×100 mL) and sat'd aq.

NaCl (1 ×100 mL). The solution was dried over magnesium sulfate, filtered, and evaporated to give the crude product. This was purified by flash chromatography eluting with 10–30% ethylacetate hexane to give the product (1.22 g, 1.97 mmole, 99%) as a pale yellow solid.

The carbonate above was dissolved in 20 mL methylene chloride, 10 mL TFA was added and the mixture was stirred at 25° C. for 16 hours. The solution was diluted with 50 mL toluene and evaporated to give the carboxylic acid as a viscous yellow oil which was azeotroped with toluene once, then dried in vacuo.

The acid prepared above (~2 mmole, 2 eq) was dissolved in 30 mL methylenechloride and this solution was added to TentaGel S $NH_2$ (3 g, 0.32 mmole/g, ~1 mmole, 1 eq). The resin was suspended by agitation then DMAP (40 mg, 0.3 mmole, 0.3 eq) and DIC (0.47 mL, 0.4 g, 3 eq) were added in that order. The resin was agitated at 25° C. for 19 hours, at which time it gave a negative Kaiser test. The resin was filtered and washed (methylenechloride 10×50 mL), then dried in vacuo.

The three other carbonate linked resin batches were prepared in an analogous manner using the reagents of Table 1–1.

c) Encoding of Step 1

One gram batches of the seven resin batches from Steps 1(a) and 1(b) with the appropriately linked N-Fmoc protected amino acid or amino alcohol were placed in seven separate synthesis vessels and each was suspended in 20 mL methylene chloride.

Stock solutions of 200 mg of $C_{12}Cl_5$, $C_{11}Cl_5$, and $C_{10}Cl_5$-linker-diazoketone (Preparation 1) were prepared in 4 mL methylenechloride. Aliquots (1 mL) of the stock solutions were used to prepare the appropriate binary coding mixtures for each of the seven resin batches. The appropriate coding mixture was added to each resin batch and the resin was agitated for 1 hour. Rhodium trifluoroacetate dimer (1 mL of a 1 mg/mL solution in methylenechloride) was added to each of the vessels and the resin was agitated at 25° C. overnight. Each resin batch was washed with methylenechloride (1×50 mL), then the batches were combined and the entire library (seven compounds) was washed with methylenechloride (10×50 mL).

d) Deprotection

N-Fmoc protecting groups were removed by washing the resin once with DMF, filtering, then suspending the resin in 60 mL 50% piperidine/DMF and agitating at room temperature for 30 min. The resin was filtered, washed (DMF (5×50 mL) and methylenechloride (10×50 mL)) and dried in vacuo.

Step 2 a) Addition of A

The dried resin from Step 1(d) was divided into 31 batches of 210 mg (~0.07 mmole), each of which was placed in a 20 mL synthesis vessel. Each of the reagents (0.25 g, >0.4 mmole, >6 eq) (Table 1–2) used in the second step of the synthesis (N-Fmoc amino acid with acid labile side chain protection where appropriate) was dissolved in 10 mL methylenechloride. HOBt (1 mL of 1 mg/mL in DMF) was added and the solutions were shaken briefly. Further DMF was added to those amino acids that had not completely dissolved. Each reagent solution was added to one of the 31 resin batches. DIC (0.2 mL, ~1 mmole) was added to each vessel and the resin was agitated at 25° C. overnight. Each of the resin batches was filtered and washed separately (DMF (1×15 mL) and methylenechloride (10×15 mL)). The resin was suspended in 10 mL methylenechloride.

b) Encoding of Step 2

Stock solutions of 160 mg of $C_9Cl_5$, $C_8Cl_5$, $C_7Cl_5$, $C_6Cl_5$, and $C_5Cl_5$-linker-diazoketone (Preparation 1) were prepared in 16 mL methylenechloride. Aliquots (1 mL) of the stock solutions were used to prepare the appropriate binary coding mixtures for each of the 31 resin batches (Table 1–2). The appropriate coding mixture was added to each of the resin batches and the resin was agitated for 30 min. Rhodium trifluoroacetate dimer (1 mL of a 1 mg/mL solution in methylenechloride) was added to each of the vessels and the resin was agitated at 25° C. overnight. Each resin batch was filtered then washed separately with methylenechloride (1×15 mL). The batches were combined and the entire library (217 compounds) was washed with methylenechloride (5×50 mL).

c) Deprotection

N-Fmoc protecting groups were removed by washing the resin once with DMF, filtering, then suspending the resin in 60 mL 50% piperidine/DMF and agitating at room temperature for 30 min. The resin was filtered, washed (DMF (5×50 mL) and methylenechloride (10×50 mL)) and dried in vacuo.

Step 3 a) Addition of Y

The dried resin from Step 2 (c) was divided into 31 batches of 150 mg (~0.05 mmole), each of which was placed in a 20 mL synthesis vessel. Each of the reagents (0.25 g, >0.4 mmole, >8 eq) used in the third step of the synthesis was dissolved in methylenechloride or DMF or a mixture of the two as appropriate (Table 1–3). Each reagent solution was added to one of the 31 resin batches, then any coreagents were added as required (see table). The resin batches were agitated at 25° C. overnight, then each was washed (DMF (1×10 mL) and methylenechloride (10×10 mL)).

b) Encoding of Step 3

Stock solutions of 200 mg of $C_4Cl_5$ and $C_3Cl_5$-linker-diazoketone (Preparation 1) were prepared in 16 mL methylenechloride. Stock solutions of 600 mg of $C_6Cl_3$, $C_5Cl_3$, and $C_4Cl_3$-linker-diazoketone (Preparation 1) were prepared in 16 mL methylenechloride. Aliquots (1 mL) of the stock solutions were used to prepare the appropriate binary coding mixtures for each of the 31 resin batches (Table 1–3). The appropriate coding mixture was added to each of the resin batches and the resin was agitated for 30 min. Rhodium trifluoroacetate dimer (1 mL of a 1 mg/mL solution in methylenechloride) was added to each of the vessels and the resin was agitated at 25° C. overnight. Each resin batch was filtered then washed separately with methylenechloride (1×15 mL). The batches were combined and the entire library (6727 compounds) was washed with methylenechloride (5×50 mL), then dried in vacuo.

c) Deprotection

The combined resins from Step 3(b) (~2 g) were suspended in 60 mL TFA/thioanisole/EDT (50/50/5) and shaken at room temperature overnight. The resins were filtered, washed (methylenechloride 10×50 mL), and dried in vacuo.

TABLE 1-1
R¹ Residues and Encoding Scheme
| R¹ | Residue | Binary Code |
|---|---|---|
| 1. | 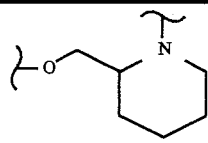 | 001 |
| 2. | 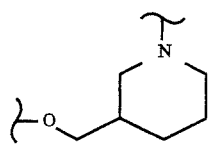 | 010 |
| 3. | 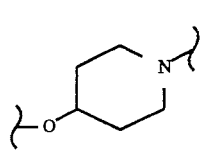 | 011 |
| 4. | 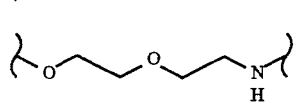 | 100 |
| 5. | 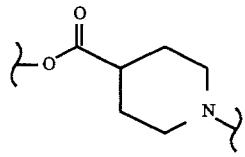 | 101 |
| 6. | 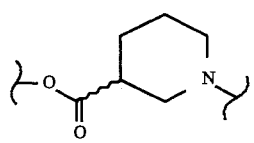 | 110 |
| 7. | 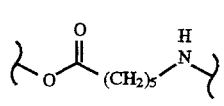 | 111 |
TABLE 1-2
A Reagents and Encoding Scheme
| | Reagent | Binary Code |
|---|---|---|
| 8. | 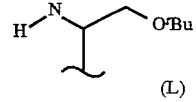 (L) | 00001 |
| 9. | 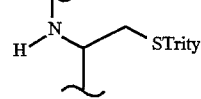 (D) | 00010 |
| 10. | 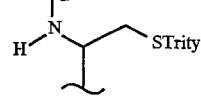 (D) | 00011 |
TABLE 1-2-continued
A Reagents and Encoding Scheme
| | Reagent | Binary Code |
|---|---|---|
| 11. | 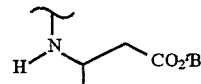 (L) | 00100 |
| 12. | 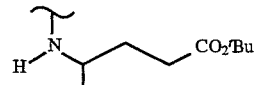 (L) | 00101 |
| 13. | 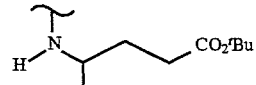 (L) | 00110 |
| 14. | 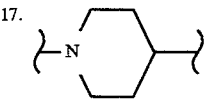 (D) | 00111 |
| 15. | 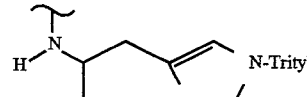 (D) | 01000 |
| 16. | 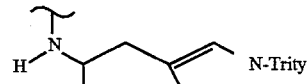 (L) | 01001 |
| 17. | 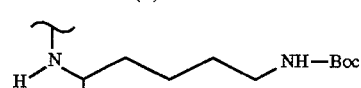 | 01010 |
| 18. | 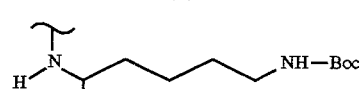 (D) | 01011 |
| 19. | 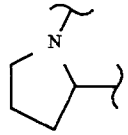 (L) | 01100 |
| 20. | 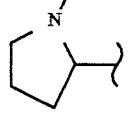 (L) | 01101 |
| 21. | 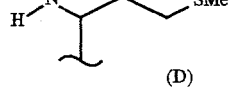 (D) | 01110 |

TABLE 1-2-continued
A Reagents and Encoding Scheme
| | Reagent | Binary Code |
|---|---|---|
| 22. | 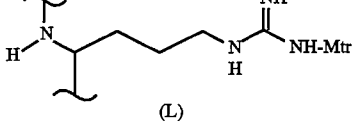 (L) | 01111 |
| 23. | 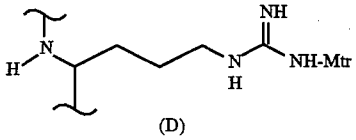 (D) | 10000 |
| 24. | 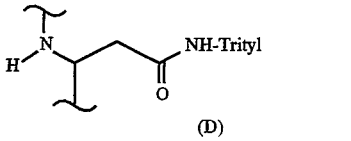 (D) | 10001 |
| 25. | 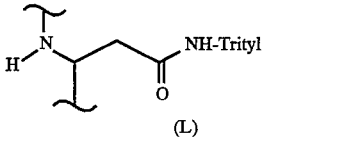 (L) | 10010 |
| 26. | 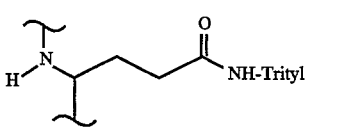 (L) | 10011 |
| 27. | 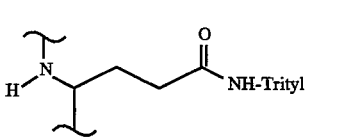 (D) | 10100 |
| 28. | 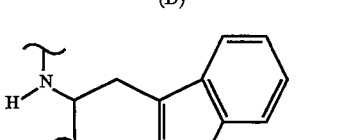 (L) | 10101 |
| 29. | 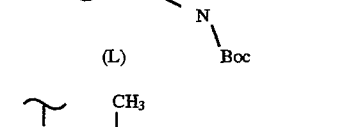 (L) | 10110 |
| 30. | 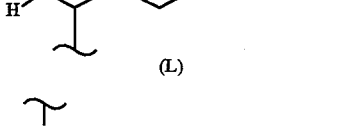 (L) | 10111 |
| 31. | 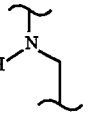 | 11000 |
| 32. | 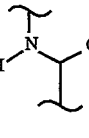 (D) | 11001 |
| 33. | 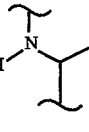 (D) | 11010 |
| 34. | 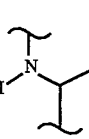 (L) | 11011 |
| 35. | 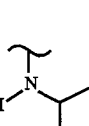 (L) | 11100 |
| 36. | 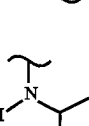 (D) | 11101 |
| 37. | 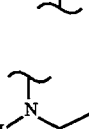 | 11110 |
| 38. | 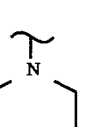 | 11111 |

TABLE 1-3

Y Reagents and Encoding Scheme

| | Y Reagent | Solvent | Co-reagent(s) | Binary Code |
|---|---|---|---|---|
| 39. | 4-sulfamoylbenzoic acid | DMF | 0.3 mL DIC, 100 mg DMAP | 00001 |
| 40. | 4-chloro-3-sulfamoylbenzoic acid | DMF | 0.3 mL DIC, 100 mg DMAP | 00010 |
| 41. | 2,4-dichloro-5-sulfamoylbenzoic acid | DMF | 0.3 mL DIC, 100 mg DMAP | 00011 |
| 42. | naphthalene-1-sulfonyl chloride | CH$_2$Cl$_2$ | 0.5 mL NEt$_3$, 100 mg DMAP | 00100 |
| 43. | naphthalene-2-sulfonyl chloride | CH$_2$Cl$_2$ | 0.5 mL NEt$_3$, 100 mg DMAP | 00101 |
| 44. | 4-chlorobenzenesulfonyl chloride | CH$_2$Cl$_2$ | 0.5 mL NEt$_3$, 100 mg DMAP | 00110 |
| 45. | 4-methylbenzenesulfonyl chloride | CH$_2$Cl$_2$ | 0.5 mL NEt$_3$, 100 mg DMAP | 00111 |
| 46. | benzenesulfonyl chloride | CH$_2$Cl$_2$ | 0.5 mL NEt$_3$, 100 mg DMAP | 01000 |
| 47. | 5-(dimethylamino)naphthalene-1-sulfonyl chloride | CH$_2$Cl$_2$/DMF (1:1) | 0.5 mL NEt$_3$, 100 mg DMAP | 01001 |
| 48. | n-BuSO$_2$Cl | CH$_2$Cl$_2$ | 0.5 mL NEt$_3$, 100 mg DMAP | 01010 |

TABLE 1-3-continued

Y Reagents and Encoding Scheme

| | Y Reagent | Solvent | Co-reagent(s) | Binary Code |
|---|---|---|---|---|
| 49. | (CH₃)₃C—C₆H₄—SO₂Cl | CH₂Cl₂ | 0.5 mL NEt₃, 100 mg DMAP | 01011 |
| 50. | (CH₃)₂CH—SO₂Cl | CH₂Cl₂ | 0.5 mL NEt₃, 100 mg DMAP | 01100 |
| 51. | PhCH₂—SO₂Cl | CH₂Cl₂ | 0.5 mL NEt₃, 100 mg DMAP | 01101 |
| 52. | 4-biphenyl-CO₂H | CH₂Cl₂ | 0.3 mL DIC, 100 mg DMAP | 01110 |
| 53. | 2-biphenyl-CO₂H | CH₂Cl₂/DMF (1:1) | 0.3 mL DIC, 100 mg DMAP | 01111 |
| 54. | 3-cyanobenzoic acid | CH₂Cl₂/DMF (1:1) | 0.3 mL DIC, 100 mg DMAP | 10000 |
| 55. | glutaric anhydride | CH₂Cl₂ | 100 mg DMAP | 10001 |
| 56. | nicotinic acid | CH₂Cl₂/DMF (1:1) | 0.3 mL DIC, 100 mg DMAP | 10010 |
| 57. | MeO—(CH₂)₅—CO₂H | CH₂Cl₂ | 0.3 mL DIC, 100 mg DMAP | 10011 |
| 58. | PhCO₂H | CH₂Cl₂ | 0.3 mL DIC, 100 mg DMAP | 10100 |
| 59. | H₃C—CH₂—CO₂H | CH₂Cl₂ | 0.3 mL DIC, 100 mg DMAP | 10101 |
| 60. | indole-3-acetic acid | CH₂Cl₂/DMF (1:1) | 0.3 mL DIC, 100 mg DMAP | 10110 |

TABLE 1-3-continued

Y Reagents and Encoding Scheme

| Y Reagent | Solvent | Co-reagent(s) | Binary Code |
|---|---|---|---|
| 61. hydantoin-CH₂-CH(CO₂H)- structure | CH₂Cl₂/DMF (1:1) | 0.3 mL DIC, 100 mg DMAP | 10111 |
| 62. imidazole-CH=C(CO₂H)- structure | CH₂Cl₂/DMF (1:1) | 0.3 mL DIC, 100 mg DMAP | 11000 |
| 63. 4-(trifluoromethyl)phenyl isocyanate | CH₂Cl₂ | | 11001 |
| 64. phenyl isocyanate | CH₂Cl₂ | | 11010 |
| 65. isopropyl chloroformate | CH₂Cl₂ | 0.5 mL NEt₃ | 11011 |
| 66. 4-chlorophenyl isocyanate | CH₂Cl₂ | | 11100 |
| 67. naphthalene-2-sulfonyl-NH-CH₂-CO₂H | Fmoc-G-OH, DIC, DMAP DMF, then piperidine/ DMF | 2-Napthalene-sulfonyl chloride, NEt₃, DMAP, CH₂Cl₂ | 11101 |
| 68. 4-biphenyl-C(O)NH-CH₂-CO₂H | Fmoc-G-OH, DIC, DMAP DMF, then piperidine/ DMF | 4-Biphenyl-carboxylic acid, DIC, DMAP, CH₂Cl₂/DMF | 11110 |
| 69. imidazolyl-CH₂-C(O)NH-CH₂-CO₂H | Fmoc-G-OH, DIC, DMAP DMF, then piperidine/ DMF | Imidazole-acetic acid, DIC, DMAP, CH₂Cl₂/DMF | 11111 |

EXAMPLE 2

6727 COMPOUND LIBRARY

The procedure of Example 1 is followed except that in Steps 1(c) and 2(b) the batches are not combined. Instead, each batch is individually deprotected and then the batches are directly divided into the appropriate number of batches for the next step.

EXAMPLE 3

EXAMPLE 1 IN 5-FOLD REDUNDANCY

The procedure of Example 1 is followed except that a total of 33,635 solid supports are used.

EXAMPLE 4

EXAMPLE 2 IN 5-FOLD REDUNDANCY

The procedure of Example 2 is followed except that a total of 33,635 solid supports are used.

EXAMPLE 5

COMPARISON OF EXAMPLES 3 AND 4

Combinatorial analyses of Examples 3 and 4 produce the following results:

| % Not Represented | | | | | |
|---|---|---|---|---|---|
| | | % Under-represented | | % Over-represented | |
| Split Syn. | Direct Div. | Split Syn. | Direct Div. | Split Syn. | Direct Div. |
| 0.657 | 0.413 | 44.0 | 42.4 | 38.4 | 38.3 |

All publications and patent applications cited herein are incorporated by reference.

What is claimed is:

1. In a process for synthesizing a combinatorial library of compounds in a plurality of reaction vessels, wherein for each step of the synthesis each of the plurality of reaction vessels is subject to unique reaction conditions such that different compounds of the library are produced by said unique reaction conditions, said library exhibiting a minimum variance in distribution of products in each vessel, which comprises the steps of (1) partitioning a set of particles into a first group of reaction vessels wherein each reaction vessel is subject to a unique set of reaction conditions, (2) repartitioning the treated particles into a second group of reaction vessels wherein each reaction vessel is again subject to a unique set of reaction conditions, and (3) repeating step (2) at least once, wherein the improvement comprises repartitioning the treated particles by directly dividing the contents of each reaction vessel into each of the succeeding reaction vessels for every step in said process, whereby the number of reaction vessels is the same as the number of unique reaction conditions at each step.

2. The process of claim 1 wherein the combinatorial library comprises peptides, oligonucleotides, or oligosaccharides, or combinations thereof.

3. The process of claim 1 wherein the combinatorial library comprises non-oligomers.

4. The process of claim 3 wherein the non-oligomers are heterocyclic, aromatics, alicyclics, aliphatics, or combinations thereof.

5. The process of claim 1 wherein the combinatorial library comprises compounds encoded with peptide or oligonucleotide tags.

6. The process of claim 1 wherein the combinatorial library comprises compounds encoded with electrophoric tags.

7. The process of claim 1 wherein each member is represented in equimolar amounts.

8. The process of claim 1 wherein step (2) is repeated 1–5 times.

* * * * *

UNITED STATES PATENT AND TRADEMARK OFFICE
CERTIFICATE OF CORRECTION

PATENT NO.: 5,663,046

DATED: September 2, 1997

INVENTOR(S): Baldwin et al.

It is certified that error appears in the above-identified patent and that said Letters Patent is hereby corrected as shown below:

Column 6, line 21, "(T´-L)q-Ŝ-C(O)-L´-I" should read --  --.

Column 8, line 34, Scheme 1, "R=Reagents 1-4" should read --$R^1$=Reagents 1-4--.

Column 12, line 35, "(abbreviated $C_5Cl_5$, $C_6Cl_5$, $C_7C_{l5}$, $C_8C_{l5}$, and $C_9C_{l5}$)" should read --(abbreviated $C_5Cl_5$, $C_6Cl_5$, $C_7Cl_5$, $C_8Cl_5$, and $C_9Cl_5$)--.

Column 12, line 41, "$C_5C_3$," should read --$C_5Cl_3$,--.

Signed and Sealed this

Thirtieth Day of June, 1998

Attest:

BRUCE LEHMAN

Attesting Officer                    Commissioner of Patents and Trademarks